United States Patent [19]

Farooq et al.

[11] 4,100,296
[45] Jul. 11, 1978

[54] DIOXOLANE DERIVATIVES

[75] Inventors: Saleem Farooq, Aesch; Friedrich Karrer, Zofingen, both of Switzerland

[73] Assignee: Ciba-Geigy Corporation, Ardsley, N.Y.

[21] Appl. No.: 748,268

[22] Filed: Dec. 7, 1976

[30] Foreign Application Priority Data

Dec. 12, 1975 [CH] Switzerland .................. 16154/75
Dec. 24, 1975 [CH] Switzerland .................. 16784/75
Nov. 15, 1976 [CH] Switzerland .................. 14351/76

[51] Int. Cl.² .............. A61K 31/335; C07D 317/10; A01N 9/28
[52] U.S. Cl. .................................... 424/278; 71/88; 260/340.5 R; 260/340.9 R
[58] Field of Search ............... 260/340.9 R; 424/278

[56] References Cited

U.S. PATENT DOCUMENTS

| 2,636,884 | 4/1953 | Tenenbaum et al. | 260/340.9 |
| 3,997,567 | 12/1976 | Kathawala | 260/340.9 |
| 4,007,280 | 2/1977 | Karrer | 424/278 |
| 4,008,327 | 2/1977 | Kathawala | 424/278 |

*Primary Examiner*—Ethel G. Love
*Attorney, Agent, or Firm*—Harry Falber

[57] ABSTRACT

Dioxolane derivatives of the formula

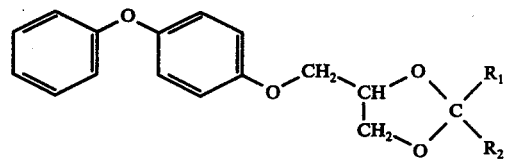

wherein
$R_1$ represents a hydrogen atom or a $C_1$-$C_4$-alkyl group,
$R_2$ represents the radical

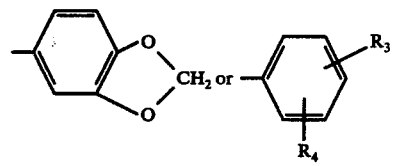

each of $R_3$ and $R_4$ independently represents a hydrogen atom, a halogen atom, a $C_1$-$C_4$-alkyl, methoxy or ethoxy group, a process for the manufacture of these compounds and a method of controlling pests, in particular in storage protection, and for regulating plant growth, which comprises the use of compositions which contain the compounds as active component.

13 Claims, No Drawings

DIOXOLANE DERIVATIVES

The present invention provides novel dioxolane derivatives, a process for their manufacture, compositions which contain these derivatives as active component, and a method of controlling pests and of regulating plant growth to facilitate the harvesting of agricultural, forestry, and garden produce, which comprises the use of the novel compounds.

The dioxolane derivatives have the formula I

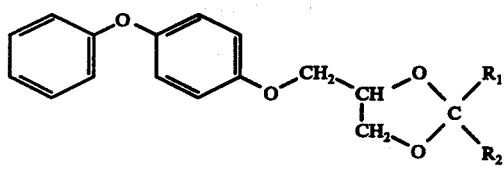

wherein
$R_1$ represents a hydrogen atom or a $C_1$–$C_4$-alkyl group,
$R_2$ represents the radical

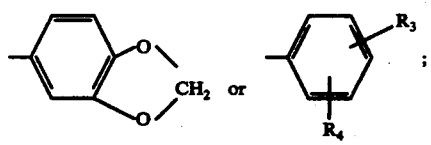

each of $R_3$ and $R_4$ independently represents a hydrogen atom, a halogen atom, a $C_1$–$C_4$-alkyl, methoxy or ethoxy group.

Particularly interesting compounds are those of the formula I in which $R_1$ represents a hydrogen atom and those in which $R_1$ represents a methyl group, whilst $R_2$ represents in particular the radical

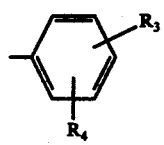

in which $R_3$ preferably represents a hydrogen atom and $R_4$ represents a halogen atom, a methyl, ethyl, isopropyl or methoxy group.

Compounds to be singled out for special mention are also those compounds of the formula I wherein $R_2$ represents the radical

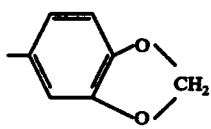

The term "halogen atom" is to be understood as meaning a fluorine, chlorine, bromine and iodine atom, preferably a chlorine atom.

An alkyl group is to be understood as meaning a straight-chain or branched unsubstituted group. Examples of such groups are: methyl, ethyl, propyl, isopropyl, n-butyl, iso-butyl, sec.-butyl and tert.-butyl.

The compounds of the formula I, which are themselves novel, can be obtained by methods which are known per se (cf. for example Houben-Weyl "Methoden der Organischen Chemie", Stuttgart, 1963, Vol. VI/3, p.199 ff.), for example as follows:

(a) By reacting the diol of the formula II

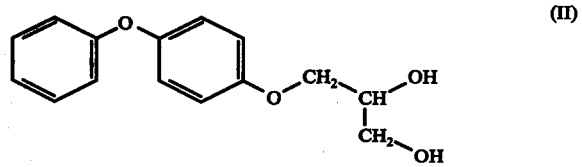

in the presence of an acid catalyst, with a carbonyl compound of the formula III

the reaction preferably being carried out with equivalent amounts of the compounds of the formulae (II) and (III), optionally with an excess of the carbonyl compound (III). The reaction temperatures vary in general between 40° and 150° C, for example between 70° and 120° C. Inert solvents can be used, for example aromatic hydrocarbons, such as benzene, toluene, xylene or halogenated hydrocarbons, such as chloroform etc. The inert solvents or diluents are advantageously used as entrainers for distilling off the water which forms during the reaction (azeotropic distillation). All acid compounds or Lewis acids which are customarily used for acetylation reactions, for example p-toluenesulphonic acid, phosphoric acid, boron trifluoride-diethyl etherate etc., can be used as catalysts.

(b) By reacting the diol of the formula II, in the presence of an acid catalyst, with an acetal or ketal compound of the formula IV

in the course of which reaction 2 moles of the corresponding alcohol are split off. In formula IV, $R_5$ represents a methyl or ethyl group, and the radicals $R_1$ and $R_2$ are as defined above. This transacetylation or transketalisation, which can be carried out in the presence of an inert solvent or diluent, takes place preferably at temperatures between 50° and 140° C, for example between 70° and 120° C. Suitable solvents or diluents are chiefly hydrocarbons, such as benzene, toluene or xylenes. The same substances can be used as catalysts as in reaction (a).

(c) By reacting the compound of the formula V

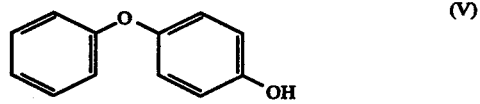

in the presence of a catalyst, with a compound of the formula VI

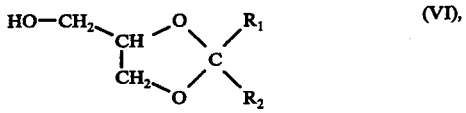

(VI)

frequently without a solvent or diluent. The reaction is carried out at a temperature of 50° to 150° C, preferably 80° to 120° C, in the presence of a condensation catalyst, for example a N,N-disubstituted carbodiimide. Preferably N,N-dicyclohexyl-carbodiimide is used and this reaction catalysed with a copper (I) salt, in particular copper (I) chloride. It is also possible to use diisopropylaminoacetylene as condensation agent (for example in benzene).

In the above described processes (a), (b) and (c) for the manufacture of compounds of the formula I, when the radicals $R_1$ and $R_2$ have different meanings mixtures of the corresponding diastereoisomers are obtained. If desired, these mixtures can be separated by physical methods, for example fractional crystallisation, gas chromatography, adsorption chromatography (layer or column chromatography) etc., to yield the respective diastereoisomeric forms.

The starting compounds of the formulae II, III, IV, V and VI are known or they can be prepared with the aid of methods which are known per se. Thus, for example, the compound of the formula II can be obtained as follows:

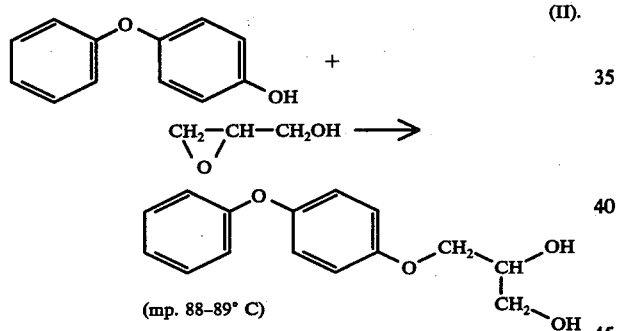

(II).

(mp. 88–89° C)

The compounds of the formula I have a broad biocidal activity and can be used for controlling a wide variety of pests which are harmful to plants and animals. The compounds of the formula I are furthermore characterised by a low toxicity, in particular to warm-blooded animals, and possess substantial advantages from the point of view of residue and environmental problems.

In particular, the compounds of the formula I are suitable for controlling insects of the families: Acrididae, Blattidae, Gryllidae, Gryllotalpidae, Tettigoniidae, Cimicidae, Phyrrhocoridae, Reduviidae, Aphididae, Delphacidae, Diaspididae, Pseudococcidae, Chrysomelidae, Coccinellidae, Bruchidae, Scarabaeidae, Dermestidae, Tenebrionidae, Curculionidae, Tineidae, Noctuidae, Lymantriidae, Pyralidae, Galleridae, Culicidae, Tipulidae, Stomoxydae, Muscidae, Calliphoridae, Trypetidae, Pulicidae and acaridae of the families: Ixodidae, Argasidae, Tetranychidae, Dermanyssidae.

Excellent effects can be obtained with the compounds of the invention when they are used to control insects which damage harvest produce and in storage protection.

The insecticidal action of the compounds of the invention can be substantially broadened and adjusted to prevailing conditions by adding other insecticides or acaricides.

Examples of suitable additives are: organic phosphorus compounds, nitrophenols and derivatives thereof, formamidines, ureas, carbamates or chlorinated hydrocarbons.

Apart from their use for controlling pests, the compounds of the formula I can be used in low rates of application for regulating the growth of many plant species.

Traditionally, the harvesting of fruit is done by hand. In the wake of rationalisation in agriculture, other methods of harvesting fruit have been suggested. To this end, a very wide variety of mechanical devices have been developed. As a rule, however, such mechanical devices damage the plants and the produce. It has been found that fruit can be made to drop either without or only with a small amount of mechanical assistance if the trees, bushes etc. are treated with the compounds of the present invention before the fruit has ripened.

The promotion of the fruit abscission can also be assisted by thinning out the young fruit by chemical means by an early application of the active compounds. This is desirable in a too pronounced, natural fruit setting such as occurs, for example, in apples, peaches or citrus fruits. The detaching of the fruit is greatly facilitated by the formation of separating tissue. This ease of detachment is of great economic importance for the mechanical harvesting of, for example, citrus fruits, olives, stone fruit, small fruits or subtropical fruits.

The active compounds are applied in the form of solid or liquid compositions both to parts of plants above or in the soil or to the soil itself. The application to the parts of plants above the soil is preferred, for which solutions or aqueous dispersions are best suited. Besides solutions and dispersions of the active compounds, dusts, granules and tracking agents are also suitable for treating the growth substrate (the soil).

The degree and nature of the abscission effect depend on different factors, in particular on the time of application in regard to the stage of development of the plant and on the application concentration. However, depending on the species of plant and the desired effect, these factors are in turn different. The amount of active compound to be applied is largely dependent on the nature of the plants to be treated and of the application (treatment of the plant or of the soil). The customary rates of application which are used for treating the soil and plants are in the range from 0.1 to 14 kg, preferably from 1 to 4 kg, of active compound per hectare of cultivated land.

It has been observed that the detachment of fruit, especially from citrus plants, is made very much easier after application of the active compounds of the formula I, whereby higher harvest yields can be attained.

The compounds of the formula I may be used as pure active substance or together with suitable carriers and/or additives. Suitable carriers and additives can be solid or liquid and correspond to the substances conventionally used in the art of formulation, for example natural or regenerated substances, solvents, dispersants, wetting agents, tackifiers, thickeners, binders and/or fertilisers.

For application, the compounds of the formula I may be processed to dusts, emulsion concentrates, granules, dispersions, sprays, to solutions, or suspensions, in the conventional formulation which is commonly employed in application technology.

The compositions according to the invention which contain compounds of the formula I are obtained in known manner by homogeneously mixing and/or grinding active substances of the formula I with the suitable carriers, with or without the addition of dispersants or solvents which are inert to the active substances.

The active substances may take, and be used in, the following forms: Dusts, tracking agents and granules (coated granules, impregnated granules and homogeneous granules).

Liquid forms:
(a) active substance concentrates which are dispersible in water: wettable powders, pastes and emulsions;
(b) solutions.

Solid forms (dusts, tracking agents) are obtained by mixing the active substances with solid carriers. Suitable carriers are, for example: kaolin, talc, bolus, loess, chalk, limestone, ground limestone, attaclay, dolomite, diatomaceous earth, precipitated silica, alkaline earth silicates, sodium and potassium aluminium silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder, residues of plant extractions, activated charcoal etc. These substances can either be used singly or in admixture with one another.

Granules can be prepared by dissolving the active substances in an organic solvent and applying the resultant solution to a granulated material, for example attapulgite, $SiO_2$, granicalcium, bentonite etc., and then evaporating the solvent.

Polymer granules can also be prepared by mixing the active compounds of the formula I with polymerisable compounds (urea/formaldehyde; diacyandiamide/formaldehyde; melamine/formaldehyde or others), whereupon a mild polymerisation is carried out which does not affect the active substances, with the granulation being effected during the gel formation. It is more advantageous to impregnate finished, porous polymer granules (urea/formaldehyde, polyacrylonitrile, polyesters and others) which have a specific surface area and a favourable predeterminable adsorption/desorption ratio, with the active substances, for example in the form of their solutions (in a low boiling solvent) and to remove the solvent. Polymer granules of this kind in the form of microgranules having a bulk density of 300 g/liter to 600 g/liter can also be manufactured with the aid of atomisers. The dusting can be carried out from aircraft over extensive areas of cultures of useful plants.

It is also possible to obtain granules by compacting the carrier with the active substance and carriers and subsequently comminuting the product.

To these mixtures can also be added additives which stabilize the active substance and/or nonionics, anionics and cationics, which, for example, improve the adhesion of the active ingredients on plants or parts of plants (tackifiers and agglutinants) and/or ensure a better wettability (wetting agents) and dispersibility (dispersing agents). Examples of suitable substances for this purpose are: olein/chalk mixture, cellulose derivatives (methyl cellulose, carboxymethyl cellulose), hydroxyethyl glycol ethers of monoalkyl and dialkyl phenols containing 5 to 15 ethylene oxide radicals per molecule and 8 to 9 carbon atoms in the alkyl moiety, lignin sulphonic acids, the alkali and alkaline earth salts thereof, polyethylene glycol ethers (carbowaxes), fatty alcohol polyethylene glycol ethers containing 5 to 20 ethylene oxide radicals per molecule and 8 to 18 carbon atoms in the fatty alcohol moiety, condensation products of ethylene oxide, propylene oxide, polyvinylpyrrolidone, polyvinyl alcohols, condensation products of urea and formaldehyde, and also latex products.

Water-dispersible active substance concentrates, i.e. wettable powders, pastes and emulsion concentrates, are compositions which can be diluted with water to the desired concentration. They consist of active substance, carrier, optionally additives which stabilize the active substance, surface-active substances and anti-foam agents and, if appropriate, solvents.

Wettable powders and pastes are obtained by mixing and grinding the active substances with dispersing agents and pulverulent carriers in suitable devices until homogeneity is attained. Suitable carriers are, for example, those already mentioned for the solid forms of application. In many cases it is advantageous to use mixtures of different carriers. As dispersing agents there can be used, for example, condensation products of sulphonated naphthalene and sulphonated naphthalene derivatives with formaldehyde, condensation products of naphthalene or naphthalenesulphonic acids with phenol and formaldehyde, as well as alkali, ammonium and alkaline earth salts of lignin sulphonic acid, in addition alkylarylsulphonates, alkali metal and alkaline earth metal salts of dibutylnapthalenesulphonic acid, fatty alcohol sulphates such as salts of sulphated hexadecanols, heptadecanols, octadecanols, and salts of sulphated fatty alcohol glycol ethers, the sodium salt of oleyl methyl tauride, ditertiary ethylene glycols, dialkyldilaurylammonium chloride and fatty acid alkali and alkaline earth salts.

Silicone oils can be used for example as anti-foam agents.

The active substances are so mixed, ground, sieved and strained with the additives mentioned above that, in wettable powders, the solid particle size of 0.02 to 0.04 mm and in pastes, of 0.03 mm, is not exceeded. Emulsion concentrates and pastes are prepared by using dispersing agents, such as those cited previously above, organic solvents, and water. Examples of suitable solvents are: alcohols, benzene, xylenes, toluene, dimethyl sulphoxide, and mineral oil fractions which boil between 120° and 350° C. The solvents must be practically odourless and inert to the active substances.

Furthermore, the compositions of the present invention which contain an active compound of the formula I can be applied in the form of solutions. For this purpose, the active compound is dissolved in suitable organic solvents, solvent mixtures or in water. Aliphatic and aromatic hydrocarbons, chlorinated derivatives thereof, alkylnapthalenes and mineral oils, singly or in admixture, can be used as organic solvents.

The content of active substance in the above described compositions is between 0.01 and 95%, in which connection it must be mentioned that higher concentrations can also be used if the compositions are applied from an aircraft or other appropriate application devices.

The active substances of the formula I can be formulated for example as follows. The parts denote parts by weight.

Dusts

The following substances are used to manufacture (a) a 5% and (b) a 2% dust:

(a)
 5 parts of active substance,
 95 parts of talc;
 2 parts of active substance,
 1 part of highly disperse silicic acid,
 97 parts of talc.

The active substances are mixed with the carriers and ground.

Granules

The following substances are used to produce 5% granules:
 5 parts of active substance,
 0.25 parts of epichlorohydrin,
 0.25 parts of cetyl polyglycol ether,
 3.50 parts of polyethylene glycol,
 91 parts of kaolin (particle size 0.3 –0.8 mm).

The active substance is mixed with epichlorohydrin and dissolved with 6 parts of acetone; the polyethylene glycol and cetyl polyglycol ether are then added. The resultant solution is sprayed on kaolin, and the acetone is subsequently evaporated in vacuo.

Wettable Powder

The following constituents are used for the preparation of (a) a 40%, (b) and (c) a 25%, and (d) a 10% wettable powder:

(a)
 40 parts of active substance,
 5 parts of sodium lignin sulphonate,
 1 part of sodium dibutylnaphthalene sulphonate,
 54 parts of silicic acid.

(b)
 25 parts of active substance,
 4.5 parts of calcium lignin sulphonate,
 1.9 parts of Champagne chalk/hydroxyethyl cellulose mixture (1:1),
 1.5 parts of sodium dibutylnaphthalene sulphonate,
 19.5 parts of silicic acid,
 19.5 parts of Champagne chalk,
 28.1 parts of kaolin, (c)
 25 parts of active substance,
 2.5 parts of isooctylphenoxy-polyoxyethyleneethanol,
 1.7 parts of Champagne chalk/hydroxyethyl cellulose mixture (1:1),
 8.3 parts of sodium aluminum silicate,
 16.5 parts of kieselguhr,
 46 parts of kaolin, (d)
 10 parts of active substance,
 3 parts of a mixture of the sodium salts of saturated fatty alcohol sulphates,
 5 parts of naphthalenesulphonic acid/formaldehyde condensate,
 82 parts of kaolin.

The active substances are homogeneously mixed, in suitable mixers, with the additives, the mixture being then ground in the appropriate mills and rollers. Wettable powders are obtained which can be diluted with water to give suspensions of the desired concentration.

Emulsifiable Concentrates

The following substances are used to produce (a) a 10% and (b) a 25% emulsifiable concentrate:

(a)
 10 parts of active substance,
 3.4 parts of epoxidised vegetable oil,
 3.4 parts of a combination emulsifier consisting of fatty alcohol polyglycol ether and alkylarylsulphonate calcium salt,
 40 parts of dimethyl formamide,
 43.2 parts of xylene;
 25 parts of active substance,
 2.5 parts of epoxidised vegetable oil,
 10 parts of alkylarylsulphonate/fatty alcohol polyglycol ether mixture,
 5 parts of dimethyl formamide,
 57.5 parts of xylene.

By diluting these concentrates with water it is possible to obtain emulsions of the required concentration.

Spray

The following ingredients are used to prepare a 5% spray:
 5 parts of active substance,
 1 part of epichlorohydrin,
 94 parts of ligroin (boiling range 160°–190° C);

The invention is further illustrated by the following Examples.

EXAMPLE 1

With stirring, 19.9 g of p-tolylaldehyde-dimethylacetal are added dropwise at 80° C in the course of approx. 30 minutes to a solution of 26 g of 1,2-dihydroxy-3-(4-phenoxy)-phenoxy-propane (prepared from 4-phenoxyphenol and glycerol glycide; m.p. 88°–89° C) and 50 ml of p-toluenesulphonic acid in 150 ml of absolute benzene. Stirring is continued at this temperature for 3 hours. The bulk of the solvent and of the methanol which has formed is subsequently distilled off. The residue is taken up in diethyl ether and the solution is washed repeatedly with a 10% solution of sodium carbonate, then with water and a saturated solution of sodium chloride. After the organic phase has been dried over sodium sulphate, the solvent is distilled off and the residue is recrystallised once from cyclohexane and then once from ligroin-toluene (2:1) to yield 4-(4-phenoxy)-phenoxymethyl-2-(p-toluyl)-1,3-dioxolane with a melting point of 69°–70° C. The following compounds of the formula I are prepared in analogous manner:

| $R_1$ | $R_2$ | Physical data |
|---|---|---|
| H | 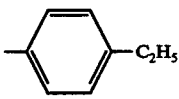 | |

-continued

| $R_1$ | $R_2$ | Physical data |
|---|---|---|
| H | 4-methylphenyl (H₃C at top, CH₃ at 4-position) | |
| H | 4-isopropylphenyl —C₆H₄—CH(CH₃)₂ | m.p.: 61–67° C |
| H | 4-tert-butylphenyl —C₆H₄—C(CH₃)₃ | |
| H | 3-Cl-4-CH₃-phenyl | |
| H | 4-methoxyphenyl —C₆H₄—OCH₃ | m.p.: 66–67° C |
| H | 4-ethoxyphenyl —C₆H₄—OC₂H₅ | $n_D^{20}$: 1.5786 |
| H | 4-chlorophenyl —C₆H₄—Cl | m.p.: 56–64° C |
| H | 4-bromophenyl —C₆H₄—Br | |
| H | 3,4-methylenedioxyphenyl (—O—CH₂—O—) | m.p.: 77–78° C |
| H | phenyl | $n_D^{20}$: 1.5841 |
| H | 3,4-dichlorophenyl | $n_D^{20}$: 1.5952 |
| —CH₃ | phenyl | m.p.: 67–69° C |
| n-C₄H₉ | phenyl | $n_D^{20}$: 1.5558 |

EXAMPLE 2

(A) Contact Action on *Dysdercus fasciatus* (larvae)

A specific amount of a 0.1% solution of active compound in acetone (corresponding to 10 mg active substance/m²) was pipetted into an aluminium dish and evenly distributed.

After evaporation of the acetone, 10 larvae of Dysdercus fasciatus in the fifth stage were put into the dishes containing feed and moist cotton wool. The dish was then covered with a perforated top.

Above about 10 days, i.e. after the untreated controls had shed and emerged fully to the adult stage, the test subjects which had developed from the larvae treated as described above were examined for the number of normal adults.

(B) Action on *Aëdes aegypti* (larvae)

Active substance concentrations of 10, 5 and 1 ppm respectively were obtained by pipetting a specific amount of a 0.1% solution of the active substance in acetone onto the surface of 150 ml of water in each of a number of beakers. After the acetone had evaporated, 30 to 40 2-day-old larvae of *Aëdes aegypti* were put into each of the beakers containing the active substance solution. Two beakers per concentration of active substance were used for the test. Then ground feed was added to the beakers, which were covered with a copper gauze top. Evaluation of mortality was made after 1, 2 and 5 days respectively. Subsequently, evaluation was made of the inhibiting action on pupation, metamorphosis, and shedding and emergence to the adult stage.

(C) Contact Action on *Tenebrio molitor* (pupae)

A specific amount of a 0.1% solution of active substance in acetone, corresponding to 10 mg active substance/m², was pipetted into an aluminium dish and evenly distributed.

After evaporation of the acetone, 10 pupae which had just shed their cocoon were placed onto the treated plate. The dish was covered with a perforated top.

After the untreated controls had emerged from the pupae cocoon as imagines, the test subjects were examined for the number of adults.

The compounds of formula I displayed good activity in the above test.

EXAMPLE 3

Action against *Ephestia kühniella*

The active substance to be tested was formulated with suitable carrier materials to a 5% dust. Then 50 g of corn meal were mixed in two beakers with a specific amount of the 5% dust preparation so as to give an active substance concentration of 0.05% in the meal.

Then 10 larvae of *Ephestia kühniella* were put into each beaker (contents: 25 g of meal). The population development was observed over a period of 8 weeks and the number of developed imagines determined.

The compounds of the formula I exhibited a good action in this test.

EXAMPLE 4

Action against *Musca domestica*

50 g of freshly prepared CSMA nutrient substrate for maggots were charged into beakers. A specific amount of a 1% acetonic solution of the respective active substance was pipetted onto the nutrient substrate present in the beakers. The substrate was then thoroughly mixed and the acetone subsequently allowed to evaporate over a period of at least 20 hours.

Then 25 1-day-old maggots of *Musca domestica* were put into each of the beakers containing the treated nutrient substrate for testing with each active substance at one of its given concentrations. After the maggots had pupated, the pupae were separated from the substrate by flushing them out with water and then deposited in containers closed with a perforated top.

Each batch of flushed out pupae was counted to determine the toxic effect of the active substance on the maggot development. The number of flies which had hatched out of the pupae was then counted after 10 days and any influence on the metamorphosis thereby determined.

The compounds of the formula I displayed good activity in this test.

EXAMPLE 5

Action against Storage Pests

Grains of wheat were treated with a dust formulation containing 5% by weight of active substance, so that an active substance concentration of 10 ppm, referred to the weight of the grains, was obtained. Then a number of 500 g portions of the treated grains were populated with 25 adult beetles of the species named hereinbelow. After an exposure time of 3 months, the number of living and dead beetles was determined in comparison with controls in untreated grains of wheat.

The compounds of the formula I exhibited a good action against *Trogoderma granarium, Sitophilus granarius, Rhyzoperta dominica, Tribolium castaneum* and *Oryzaephilus surinamensis.*

EXAMPLE 6

Action as Citrus Fruit Abscission Agent

Branches of orange trees (variety Hamlin, Pineapple or Valencia), which bore at least 20 oranges, were sprayed shortly before harvesting with solutions which contained a compound of the formula I in a concentration of 250 to 4000 ppm as active component. Evaluation was made 7 days later using two different systems:
 (a) Measuring the amount of force needed to pick the fruit and determining the reduction of the force in comparison with untreated controls.
 (b) Determining the percentage of fallen fruit (without shaking the plant) in comparison with untreated controls (0%).

The treatment of the plants with active compounds of the formula I of the present invention resulted in a substantial increase in the formation of separation tissue layers at the stems of the fruit. The amount of force needed to pick and remove the fruit from the branch was correspondingly substantially reduced. In many cases, the treatment with the active compounds of the formula I resulted in an abscission of most of the fruit on a branch.

The compounds of the formula I exhibited in this test a good action as citrus fruit abscission agents.

What is claimed is:

1. A compound of the general formula I

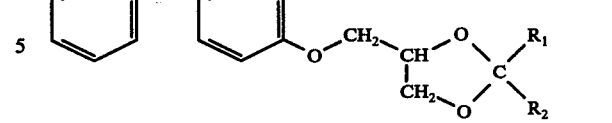

wherein
 $R_1$ represents a hydrogen atom or a $C_1$-$C_4$-alkyl group,
 $R_2$ represents the radical

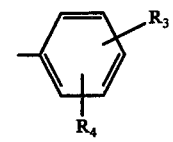

each of $R_3$ and $R_4$ independently represents a hydrogen atom, a halogen atom, a $C_1$-$C_4$-alkyl, methoxy or ethoxy group.

2. A compound according to claim 1, wherein $R_1$ in formula I represents a hydrogen atom.

3. A compound according to claim 2, wherein in formula I
 $R_1$ represents a methyl group,
 $R_2$ represents the radical

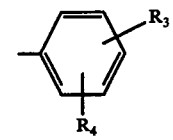

$R_3$ represents a hydrogen atom and
 $R_4$ represents a halogen atom, a methyl, ethyl, isopropyl or methoxy group.

4. A compound according to claim 2 of the formula

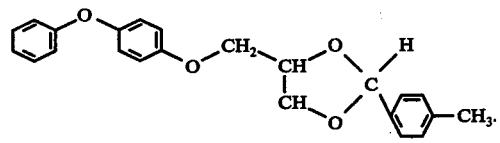

5. A compound according to claim 2 of the formula

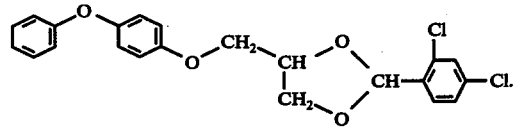

6. A compound according to claim 2 of the formula

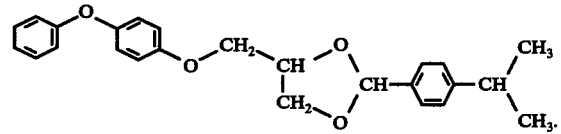

7. A compound according to claim 2 of the formula

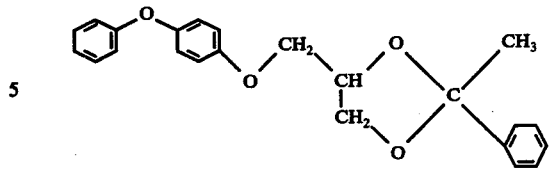

10. A compound according to claim 1 of the formula

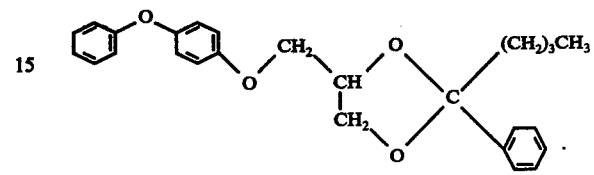

11. An insecticidal and acaricidal composition comprising as active ingredient an insecticidally and acaricidally effective amount of a compound of the general formula I as defined in claim 1 in admixture with a suitable carrier therefor.

12. A method for controlling insects and acarids, which comprises applying to the locus thereof an insecticidally and acaricidally effective amount of at least one compound of the general formula I as defined in claim 1.

13. A method according to claim 12, wherein the insects and acarids to be controlled are storage pests.

* * * * *

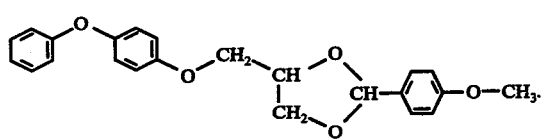

8. A compound according to claim 2 of the formula

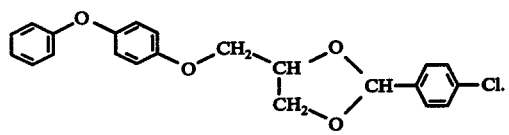

9. A compound according to claim 3 of the formula